March 16, 1948. E. PRUSHEK Plant Pat. 790
CHRYSANTHEMUM PLANT
Filed Dec. 16, 1946
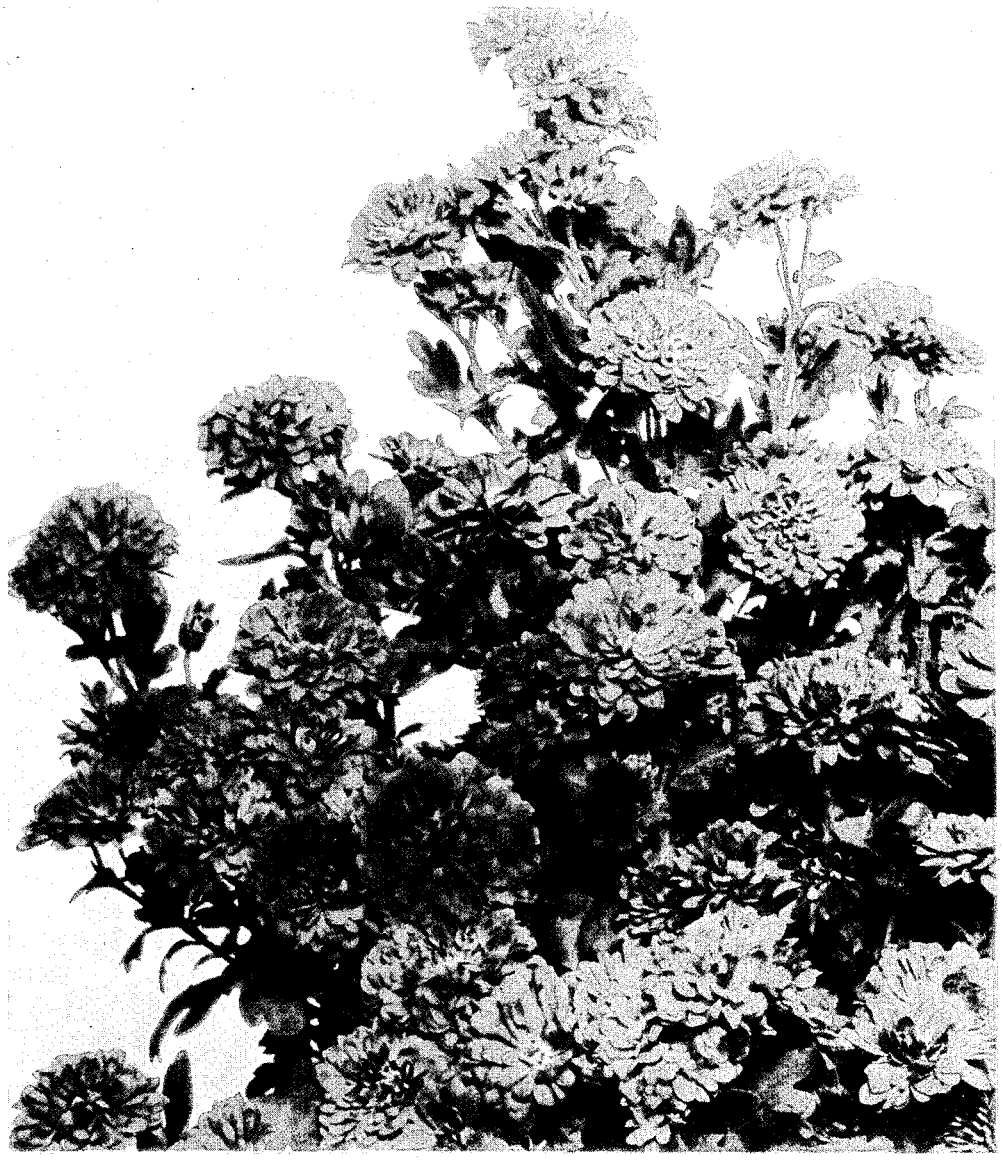
Inventor.
E. Prushek
By: Robert Cobb
Attorneys.

Patented Mar. 16, 1948 Plant Pat. 790

UNITED STATES PATENT OFFICE

790

CHRYSANTHEMUM PLANT

Emil Prushek, Niles, Mich., assignor to Jackson & Perkins Company, Newark, N. Y., a corporation of New York Application December 16, 1946, Serial No. 716,483

1 Claim. (Cl. 47—60)

The present invention relates to a new and distinct variety of chrysanthemum plant, the result of a definite breeding sequence having as its primary object the improvement of certain characteristics of the parent varieties.

In seeking the results, I crossed the known "Jewel" variety of chrysanthemum with an unnamed, red, Korean seedling, thus producing a "Jewel" type plant and flower with characteristics of the Koreans in growth and color.

More specifically, this new variety is a distinctly hardy seedling of the "Jewel" type, but having more rigid stems and flatter flowers of a new color wholly unlike that of the parent "Jewel" variety. The "Jewel" type chrysanthemums known to the trade today have not been able to survive the rigid climate where this new variety was originated and do not possess the characteristic freedom of growth and bloom of the new variety.

Furthermore, this new chrysanthemum is a better propagator than the "Jewel" type, producing many underground stems. However, it is most nearly like the "Pink Jewel," differing therefrom in the following respects:

(1) The new variety has more wiry flower-producing stems;

(2) The blossoms of the new variety when matured are flatter; and (3) The color of the new variety is distinct.

Thus, this invention adds a new color to the "Jewel" group, a hardier variety of plant and a more permanent one in areas where the "Jewel" variety will not exist.

A further notable characteristic of this new variety is the habit of mature plants sending up many stems with clusters of blooms at the top, and later blooms forming in the axils of the leaves along the stem, creating a long blooming period.

Asexual reproduction of this new variety shows the foregoing characteristics come true to form and are established.

The accompanying drawing shows a group of the flowers of this new variety in mid-October at Newark, New York, where the observations were prepared for this disclosure.

The following is a detailed description of this new variety, the color terminology being in accordance with Ridgway's Color Standard:

Growth habits: Bushy plants about 2′ tall, produce many branchy upright stems; heavy foliage with flowers set closely above the foliage; very winter hardy and a good compact plant.

Blooming season: Blooms from October 1st and continues in this climate until frost destroys it. Peak of bloom is October 20th. Continuation of bloom is developed by succession of flowering shoots starting from leaves below the top clusters.

Stems: Slender, wiry and stiff.

*Petiole.*—1½–¾″.

Foliage:

*Color.*—Elm Green, Plate 17, on upper side. Light Cress Green, Plate 31, on under side.

*Size.*—Small.

*Shape.*—Palmately divided with deep lobes and rounded tips of the lobes. In the older foliage, the deep incisions are serrated but are close and give almost the impression of a full leaf.

Flower: Bud rounded; opens flat very slowly.

*Form.*—Composite flower—most flowers completely double. Some early flowers show slight yellow center, Primuline Yellow, Plate 16. The outside ray florets or petals are about 1″ in length shortening in length to the center ray florets to about ½″ in length, creating a flat flower.

*Color.*—Open flower, Pomegranate Purple, Plate 12, with some of the center petals showing Armaranth Purple, Plate 12. The base of the petal is Sulphur Yellow, Plate 5. Reverse—Pale Amaranth Pink, Plate 12, the edges flushed with Amaranth Purple, Plate 12. The color effect is brilliant and rich and is enhanced by the lighter reverse of the petals.

*Size.*—About 2″.

Stem:

*Flowering shoot.*—Color—Hay's Brown, Plate 39, overlaid with Dark Green, Plate 18.

*Woody shoot.*—Color—Saccardo's Umber, Plate 29.

Fragrance: Sweet chrysanthemum.

Lasting quality as cut flower: Excellent for both flower and retention of color.

I claim:

A new and distinct variety of chrysanthemum plant characterized as to novelty by its hardiness and permanence, freedom of growth, its habit of producing many underground stems and great numbers of wiry flower-producing stems, its habit in mature plants of sending up many stems with clusters of blooms at the top and formation of later blooms in axils of the leaves along the stems, thereby creating a long blooming period, the flat shape of the blossoms and the distinctive color of such blossoms, substantially as shown and described.

EMIL PRUSHEK.